United States Patent
Clayton et al.

(10) Patent No.: US 8,911,409 B2
(45) Date of Patent: Dec. 16, 2014

(54) LIGHT FOR ORAL ANESTHESIA INJECTION SYRINGE

(71) Applicants: M. Wade Clayton, Germantown, TN (US); Jimmy E. Brown, Bartlett, TN (US)

(72) Inventors: M. Wade Clayton, Germantown, TN (US); Jimmy E. Brown, Bartlett, TN (US)

( * ) Notice: Subject to any disclaimer, the term of this patent is extended or adjusted under 35 U.S.C. 154(b) by 0 days.

(21) Appl. No.: 13/750,111

(22) Filed: Jan. 25, 2013

(65) Prior Publication Data

US 2014/0212830 A1 Jul. 31, 2014

(51) Int. Cl.
*A61M 5/00* (2006.01)
*A61B 1/24* (2006.01)

(52) U.S. Cl.
CPC .......................................... *A61B 1/24* (2013.01)
USPC ............................................ 604/181; 433/29

(58) Field of Classification Search
USPC ............. 604/181, 187, 218, 264, 116; 433/29
See application file for complete search history.

(56) References Cited

U.S. PATENT DOCUMENTS

| | | | | |
|---|---|---|---|---|
| 2,437,697 | A * | 3/1948 | Kalom | 600/550 |
| 4,040,419 | A * | 8/1977 | Goldman | 604/187 |
| 6,159,161 | A * | 12/2000 | Hodosh | 600/561 |
| 6,595,962 | B1 | 7/2003 | Perthu | |
| 7,351,231 | B2 * | 4/2008 | Young | 604/264 |
| 7,896,838 | B2 * | 3/2011 | Devega | 604/116 |
| 8,371,848 | B2 * | 2/2013 | Okawa et al. | 433/29 |
| 2005/0080384 | A1 | 4/2005 | Green, Jr. | |
| 2008/0234625 | A1 | 9/2008 | Dacquay et al. | |
| 2009/0216193 | A1 | 8/2009 | Schriver et al. | |
| 2010/0069851 | A1 | 3/2010 | Vad et al. | |

FOREIGN PATENT DOCUMENTS

| | | |
|---|---|---|
| DE | 3322923 A1 | 1/1985 |
| DE | 102006018143 A1 | 10/2007 |
| EP | 238778 A2 * | 9/1987 |
| JP | 2001137341 A | 5/2001 |

OTHER PUBLICATIONS

International Searching Authority of US PCT Receiving Office, Notification of Transmittal of the International Search Report and the Written Opinion of the International Searching Authority or Declaration, Form PCT/ISA/220 for International Application PCT/US2014/013251 (transmitted May 12, 2014; published Jul. 31, 2014) World Intellectual Property Organization, Geneva, Switzerland.

(Continued)

*Primary Examiner* — Theodore Stigell
(74) *Attorney, Agent, or Firm* — Walker, McKenzie & Walker, P.C.

(57) ABSTRACT

A light for use with an oral anesthesia syringe that is received into a passageway of a barrel of the light. When the syringe is received into a first opening in a proximal end of the barrel's passageway, the needle of the syringe extends through a second opening at the proximal end of the barrel. At least one lamp and preferably a plurality of lamps at the distal end of the barrel illuminate the needle and the interior of a patient's mouth. A battery is included in the light for powering the lamps. The insertion of the syringe into the barrel closes a pair of contacts to cause the battery to power the lamps, or the battery may be removed to remove power from the lamps.

4 Claims, 2 Drawing Sheets

(56) References Cited

OTHER PUBLICATIONS

International Searching Authority of US PCT Receiving Office, International Search Report, Form PCT/ISA/210 for International Application PCT/US2014/013251 (transmitted May 12, 2014; published Jul. 31, 2014) World Intellectual Property Organization, Geneva, Switzerland.

International Searching Authority of US PCT Receiving Office, Search History for International Search Report for International Application PCT/US2014/013251 (transmitted May 12, 2014; published Jul. 31, 2014) World Intellectual Property Organization, Geneva, Switzerland.

International Searching Authority of US PCT Receiving Office, Written Opinion of the International Searching Authority, Form PCT/ISA/237 for International Application PCT/US2014/013251 (transmitted May 12, 2014; published Jul. 31, 2014) World Intellectual Property Organization, Geneva, Switzerland.

\* cited by examiner

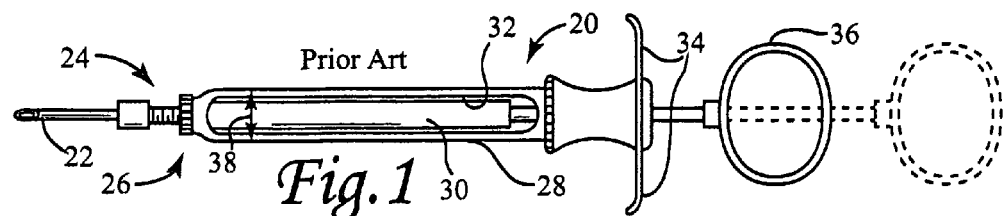
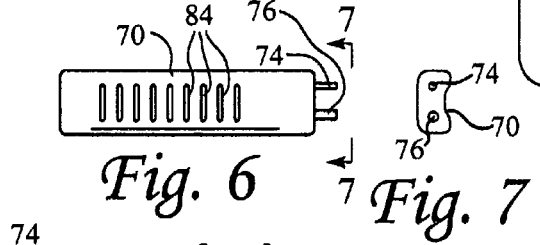
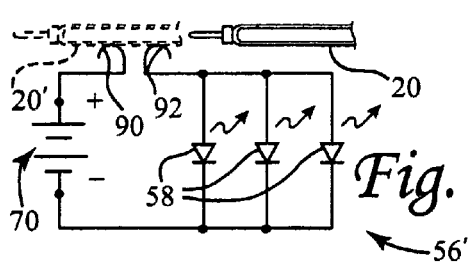
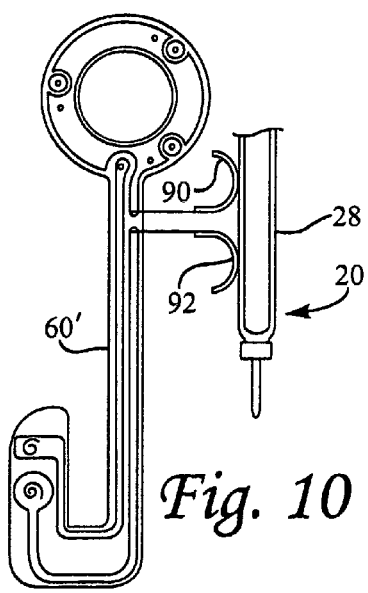

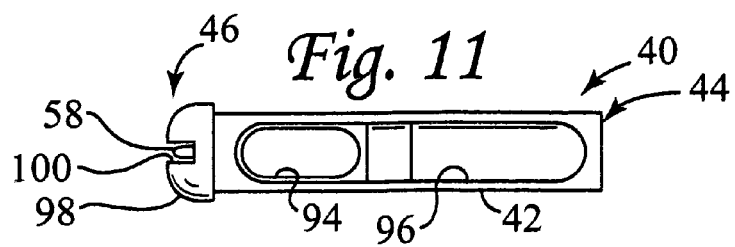
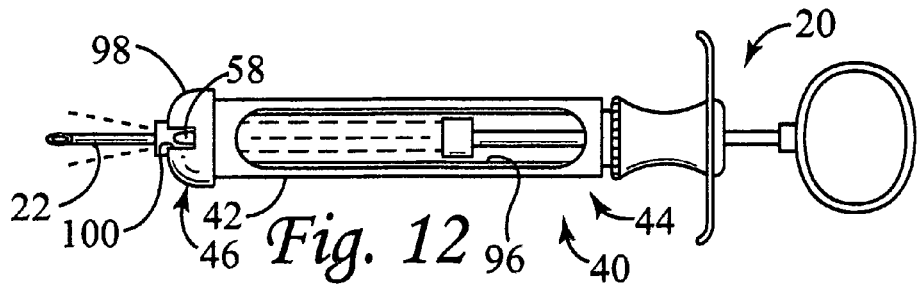
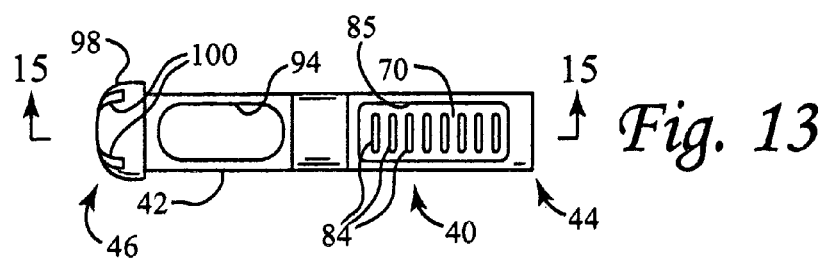
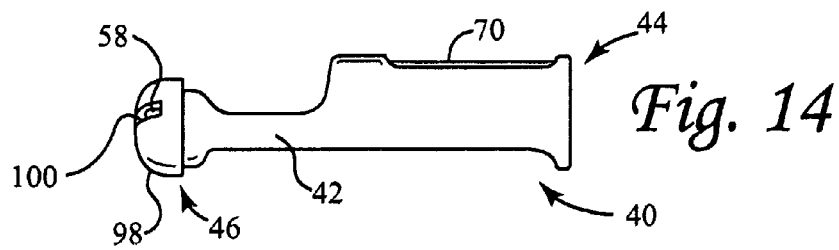
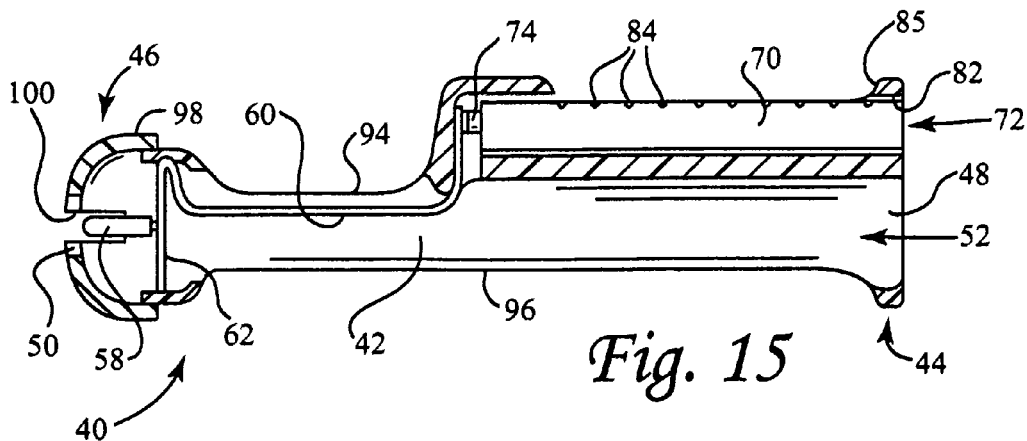

US 8,911,409 B2

LIGHT FOR ORAL ANESTHESIA INJECTION SYRINGE

CROSS REFERENCE TO RELATED APPLICATIONS

Not applicable.

STATEMENT REGARDING FEDERALLY SPONSORED RESEARCH OR DEVELOPMENT

Not applicable.

REFERENCE TO COMPACT DISC(S)

Not applicable.

BACKGROUND OF THE INVENTION

1. Field of the Invention

The present invention relates, in general, to the administration of oral anesthesia into a patient's mouth using a syringe, and, in particular, to lighting of the interior of a patient's mouth during the administration of oral anesthesia.

2. Information Disclosure Statement

It is well-known for dentists to use prior art oral anesthesia injection syringes, such as the prior art syringe shown in FIG. 1, to anesthetize a patient's mouth during dental surgery. A problem is that access to the inside of a patient's mouth is limited by the size of the patient's mouth opening, and it is difficult to adequately illuminate the inside of the patient's mouth so that the dentist can view the injection site during application of the anesthesia. Typically a light mounted on a movable arm is used to illuminate the inside of the patient's mouth, but the dentist's head and hands can impede illumination of the inside of the patient's mouth by the light. Also, when the dentist moves to various injection sites inside the patient's mouth, the light on the movable arm may have to be repositioned between injections so as to provide sufficient illumination inside the patient's mouth.

It is therefore desirable to have a light inside the patient's mouth that directly illuminates the desired injection sites as the oral anesthesia injection syringe is moved from one injection site to another. It is further desirable to provide a "hands free" means of lighting the inside of the patient's mouth that moves with the oral anesthesia injection syringe and that does not require an additional hand to manage the positioning of the lighting of the inside of the patient's mouth.

BRIEF SUMMARY OF THE INVENTION

The present invention is a light for use with an oral anesthesia syringe that is received into a passageway of a barrel of the light. When the syringe is received into a first opening in a proximal end of the barrel's passageway, the needle of the syringe extends through a second opening at the proximal end of the barrel. At least one lamp and preferably a plurality of lamps at the distal end of the barrel illuminate the needle and the interior of a patient's mouth. A battery is provided in the light for powering the lamps. The insertion of the syringe into the barrel closes a pair of contacts to cause the battery to power the lamps, or the battery may be removed in order to remove power from the lamps.

It is an object of the present invention to provide illumination of the needle of an oral anesthesia syringe and of the anesthesia injection site within a patient's mouth. It is a further object of the invention to provide self-contained "hands free" illumination within the patient's mouth that moves together with the anesthesia syringe, without having cords or wires that extend out of the patient's mouth to an external power source.

BRIEF DESCRIPTION OF THE SEVERAL VIEWS OF THE DRAWING

FIG. 1 is a side view of a prior art oral anesthesia injection syringe for use with the present invention.

FIG. 2 is a front view of the distal end of the present invention.

FIG. 3 rear view of the proximal end of the present invention with the battery inserted.

FIG. 4 is a plan view of a first side of the first embodiment of the flexible circuitry of the present invention.

FIG. 5 is a plan view of a second side of the first embodiment of the flexible circuitry of the present invention.

FIG. 6 is a side view of the battery of the present invention, removed from the battery compartment.

FIG. 7 is an end view of the battery of the present invention showing the battery contacts, taken substantially along the line 7-7 shown in FIG. 6.

FIG. 8 is a schematic of the present invention using the first embodiment of the flexible circuitry.

FIG. 9 is a schematic of the present invention using the second embodiment of the flexible circuitry, showing the circuit being completed by the metal barrel of the oral anesthesia injection syringe.

FIG. 10 is a plan view of the second side of the second embodiment of the flexible circuitry of the present invention, showing the circuit being completed by the metal barrel of the oral anesthesia injection syringe.

FIG. 11 is a bottom view of the present invention, taken substantially along the line 11-11 shown in FIG. 2.

FIG. 12 is another bottom view of the present invention, similar to FIG. 11 but with the oral anesthesia injection syringe being inserted therewithin for use in combination with the present invention.

FIG. 13 is top view of the present invention, taken substantially along the line 13-13 shown in FIG. 2.

FIG. 14 is side view of the present invention, taken substantially along the line 14-14 shown in FIG. 2. The view from the other side is substantially a mirror image of FIG. 14.

FIG. 15 is a side sectional view of the present invention showing the internal structure, taken substantially along the line 15-15 shown in FIG. 13.

DETAILED DESCRIPTION OF THE INVENTION

FIG. 1 shows a typical well-known prior art oral anesthesia syringe 20 such as would be used with the present invention. A suitable oral anesthesia injection syringe for use with the present invention is the well-known oral anesthesia injection syringe sold by Patterson Dental Supply, Inc., 1031 Mendota Heights Rd., St. Paul, Minn. 55120, U.S.A. The syringe 20 typically has a hypodermic needle 22 that is threadedly received onto a fitting 24 at the front or distal end 26 of the tubular body 28 of the syringe 20. A glass vial 30 of a local anesthetic is received into the body 28, and elongated side openings 32 are provided in the body 28 so that the amount of anesthetic within vial 30 can be observed. Finger grips 34 are provided for the dentist's fingers, and a thumb-operated plunger 36 is pushed into the vial 30 to cause injection of the anesthetic through the hypodermic needle 22, with an outer position of plunger 36 being shown in dotted outline. The parts of syringe 20 are typically made of stainless steel so that the syringe 20 may be sterilized in an autoclave. The tubular body 28 of the syringe 20 has a certain body outer diameter 38, typically about 10 mm.

FIGS. 2-15 of the drawings show the structure of the light 40 of the present invention, with FIGS. 9 and 10 showing an alternate embodiment, described hereinbelow, of the circuitry.

Light 40 includes a barrel 42 having a proximal end 44 and a distal end 46, and barrel 42 has a first opening 48 at proximal end 44 and a second opening 50 at distal end 46. Barrel 42 further has a longitudinal passageway 52 therethrough from first opening 48 to second opening 50, with passageway 52 having a transverse inner diameter 54 larger than the certain body outer diameter 38, for closely receiving the tubular body 28 of syringe 20 therewithin, with the tubular body 28 of syringe 20 extending through the first opening 48 and with the needle 22 extending out of the second opening 50 as best seen in FIG. 12. Preferably the transverse inner diameter 54 is about 1 mm or so larger than the certain body outer diameter 38 so that the syringe 20 will be frictionally retained within the passageway 52 of light 40. It will be understood that first opening 48, second opening 50, and passageway 52 are preferably co-axial on the longitudinal axis of barrel 42.

Light 40 further includes an electrical circuit 56 including at least one lamp 58 and preferably a plurality of lamps 58, such as the three light emitting diode ("LED") lamps shown in the preferred embodiments of light 40, proximate the distal end 46 of barrel 42, preferably encircling second opening 50 so as to fully illuminate the needle 22 and the anesthesia injection site in the patient's mouth. Electrical circuit 56 preferably includes a printed circuit pattern on a piece of flexible mylar 60 having a ring 62 with a center hole 64 to allow the needle of the syringe 22 to pass therethrough. Each lamp 58 is respectively mounted within a pair of holes 66, 68 in ring 62 that complete the circuit to a battery 70. Battery 70 is preferably rechargeable, as by putting battery 70 in a well-known battery charger, and is received in a battery compartment 72 of barrel 42. Battery 70 has a pair of contacts 74, 76 that contactingly and matingly engage contacts 78, 80 on the mylar circuitry. Battery 70 is preferably asymmetrically shaped to match the opening 82 of compartment 72 so that battery 70 can only be inserted correctly into compartment 72, and a plurality of small transverse channels 84 are preferably provided on an outer surface of battery 70 for ease of removal of the battery 70 as by engaging channels 84 with a user's fingernail through an access opening 85 into battery compartment 72. If desired, contacts 78, 80 on the mylar circuitry may be provided with springs 86, 88 to provide better contact with contacts 74, 76 of battery 70.

In the first embodiment 56 of the electrical circuit, power is applied to lamps 58 when the battery 70 is inserted into the battery compartment 72, thereby completing the circuit as battery contacts 74, 76 connectingly engage with contacts 78, 80 on the mylar circuitry. Likewise, power is removed from lamps 58 when the battery 70 is removed from the battery compartment 72.

An alternate or second embodiment 56' of the electrical circuit is shown in FIGS. 9 and 10, in which a modified version 60' of the mylar circuitry is used. It shall be understood that many aspects of the two preferred embodiments of the electrical circuits 60, 60' are substantially the same, and only the differences will be treated in detail, it being understood that similar structural features of the two embodiments perform similar functions.

In the second embodiment 56' of the electrical circuit, the electrical circuit 56' includes a pair of contacts 90, 92, preferably leaf spring contacts as shown, interposed between battery 70 and lamps 58. Contacts 90, 92 have a first condition, when the tubular body 28 of syringe 20 is not received within passageway 52, in which there is no electrical continuity between contacts 90, 92 (see solid outline of syringe 20 in FIG. 9), and a second condition, when the tubular body 28 of syringe 20 is received within passageway 52 (see dotted outline of syringe 20' in FIG. 9, and solid outline of syringe 20 in FIG. 10), in which there is caused to be electrical continuity between contacts 90, 92. Preferably this second condition of electrical continuity is made by the metal of tubular body 28 of syringe 20 completing the circuit between contacts 90, 92 and causing current to flow between contacts 90 and 92 through the conducting metal of tubular body 28, but the electrical continuity may be caused by mechanical engagement of tubular body 28 with one or both of contacts 90, 92 so as to cause contacts 90 and 92 to directly engage each other for current flow therebetween.

Preferably, the barrel 42 may include one or more elongated viewing openings 94, 96 so that the amount of anesthetic within vial 30 of syringe 20 can be observed during administration of local anesthesia to the patient. A cap 98 is preferably included at the distal end 46 of barrel 42 with there being a slot 100 in cap 98 in alignment with each lamp 58 to allow illumination from lamps 58 to pass to the anesthesia site and to the needle 22. Light 40 is preferably constructed of materials allowing disinfecting of the light before and after use.

To use the light of the present invention, the battery 70 is first charged in a well-known battery charger and then is inserted into the battery compartment 72. The hypodermic needle 22 is threadedly received onto fitting 24, and a vial 30 of anesthetic is placed within the syringe 20, and the syringe 20 is then inserted into and received within the passageway 52 of the light 40, with the tubular body 28 of the syringe 20 extending through the first opening 48 and with hypodermic needle 22 extending out of second opening 50. The lamps 58 will illuminate the needle 22 and the anesthesia injection site within the patient's mouth as the syringe 20 is used.

INDUSTRIAL APPLICABILITY

The light of the present invention has industrial applicability when used with an oral anesthesia injection syringe in that it illuminates the needle and the interior of a patient's mouth during injection of an oral anesthetic. The light is self-contained and unobtrusive and permits "hands free" operation, following the needle as the syringe is moved within the patient's mouth.

Although the present invention has been described and illustrated with respect to a preferred embodiment and a preferred use therefor, it is not to be so limited since modifications and changes can be made therein which are within the full intended scope of the invention.

We claim:

1. In combination, an oral anesthesia injection syringe having a hypodermic needle and having a tubular body with a certain body outer diameter, and a light, said light comprising:
   (a) a barrel having a proximal end and a distal end, said barrel having a first opening at said proximal end and a second opening at said distal end and a longitudinal passageway through said barrel from said first opening to said second opening, said passageway having a transverse inner diameter larger than said certain body outer diameter; and (b) an electrical circuit including:
  i. a plurality of lamps proximate said distal end of said barrel and encircling said second opening; and
  ii. a battery received into a compartment of said barrel for powering said plurality of lamps;
said tubular body of said syringe being received within said passageway with said tubular body of said syringe extending through said first opening and with said needle extending out of said second opening, with said plurality of lamps, when powered by said battery, illuminating said needle and an injection site of said needle.

2. The light as recited in claim 1, in which said electrical circuit further includes a pair of contacts interposed between said battery and said plurality of lamps, said pair of contacts being caused to have electrical continuity therebetween by said tubular body of the syringe being received within said passageway.

3. A light for use with an oral anesthesia injection syringe having a hypodermic needle and having a tubular body with a certain body outer diameter, said light comprising:
  (a) a barrel having a proximal end and a distal end, said barrel having a first opening at said proximal end and a second opening at said distal end and a longitudinal passageway through said barrel from said first opening to said second opening, said passageway having a transverse inner diameter larger than said certain body outer diameter for receiving the tubular body of the syringe within said passageway with the tubular body of the syringe extending through said first opening and with the needle extending out of said second opening; and
  (b) an electrical circuit including:
    i. a plurality of lamps proximate said distal end of said barrel and encircling said second opening; and
    ii. a battery received into a compartment of said barrel for powering said plurality of lamps;
with said plurality of lamps, when powered by said battery with said tubular body of said syringe being received within said passageway with the tubular body of the syringe extending through said first opening and with the needle extending out of said second opening, illuminating said needle and an injection site of said needle.

4. The light as recited in claim 3, in which said electrical circuit further includes a pair of contacts interposed between said battery and said plurality of lamps, said pair of contacts having a first condition in which there is no electrical continuity between said contacts when the tubular body of the syringe is not received within said passageway, and having a second condition in which there is caused to be electrical continuity between said contacts when the tubular body of the syringe is received within said passageway.

* * * * *